(12) United States Patent
Miller (10) Patent No.: US 8,043,264 B2
(45) Date of Patent: *Oct. 25, 2011

(54) SHEATH

(76) Inventor: Stuart H. Miller, Clifton, NJ (US)

(*) Notice: Subject to any disclaimer, the term of this patent is extended or adjusted under 35 U.S.C. 154(b) by 329 days.

This patent is subject to a terminal disclaimer.

(21) Appl. No.: 12/285,345

(22) Filed: Oct. 2, 2008

(65) Prior Publication Data

US 2009/0099549 A1    Apr. 16, 2009

Related U.S. Application Data (63) Continuation-in-part of application No. 12/078,483, filed on Apr. 1, 2008, which is a continuation-in-part of application No. 11/147,390, filed on Jun. 8, 2005.

(60) Provisional application No. 60/577,601, filed on Jun. 8, 2004, provisional application No. 60/578,308, filed on Jun. 10, 2004, provisional application No. 60/579,233, filed on Jun. 15, 2004.

(51) Int. Cl.
*A61B 5/00* (2006.01)
*A61M 29/00* (2006.01)
*A61M 5/178* (2006.01)
*A61M 25/00* (2006.01)

(52) U.S. Cl. ............ 604/164.06; 600/585; 604/104; 604/158; 604/161; 604/164.13; 604/264

(58) Field of Classification Search .......... 600/171–172, 600/585; 604/104–109, 117, 146.06, 158–180, 604/264–279, 523–539, 284–288.04

See application file for complete search history.

(56) References Cited

U.S. PATENT DOCUMENTS

| | | | |
|---|---|---|---|
| 4,565,545 A * | 1/1986 | Suzuki | 604/164.06 |
| 4,850,960 A * | 7/1989 | Grayzel | 604/510 |
| 4,895,564 A | 1/1990 | Farrell | |
| 4,961,729 A | 10/1990 | Vaillancourt | |
| 4,994,027 A * | 2/1991 | Farrell | 604/510 |
| 5,057,083 A * | 10/1991 | Gellman | 604/164.1 |
| 5,354,537 A * | 10/1994 | Moreno | 422/100 |
| 5,688,246 A * | 11/1997 | Waitz et al. | 604/164.11 |
| 5,743,874 A | 4/1998 | Fischell et al. | |
| 6,053,904 A | 4/2000 | Scribner et al. | |
| 6,106,540 A | 8/2000 | White et al. | |
| 6,336,914 B1 | 1/2002 | Gillespie, III | |
| 6,663,595 B2 | 12/2003 | Spohn et al. | |
| 6,692,482 B2 | 2/2004 | Heller et al. | |
| 7,141,059 B2 | 11/2006 | Duchamp et al. | |

* cited by examiner

*Primary Examiner* — Max Hindenburg
*Assistant Examiner* — John Pani
(74) *Attorney, Agent, or Firm* — Welsh Flaxman & Gitler LLC (57) ABSTRACT

A sheath shaped and dimensioned for reducing trauma and easing insertion thereof includes an inner sheath member shaped and dimensioned to fit around a guidewire in a manner permitting relative movement, the inner sheath member including an inner sheath tip having a primary bevel and a circumferential conical surface. The sheath also includes an outer sheath member shaped and dimensioned to fit around the inner sheath member in a manner permitting relative movement. The outer sheath member includes an outer sheath tip having a primary bevel and a circumferential conical surface.

8 Claims, 6 Drawing Sheets

SHEATH

CROSS REFERENCE TO RELATED APPLICATIONS

This application is a continuation-in-part of U.S. patent application Ser. No. 12/078,483, entitled "Sheath", filed Apr. 1, 2008, which is currently pending, which is a continuation-in-part of U.S. patent application Ser. No. 11/147,390, entitled "Sheath", filed Jun. 8, 2005, which is currently pending, which is based upon U.S. Provisional Patent Application Ser. Nos. 60/577,601, entitled "Sheath", filed Jun. 8, 2004, 60/578,308, entitled "Sheath", filed Jun. 10, 2004, and 60/579,233, entitled "Sheath", filed Jun. 15, 2004.

BACKGROUND OF THE INVENTION

1. Field of the Invention

The invention relates to a guidewire sheath. Mote particularly, the invention relates to a guidewire sheath having inner and outer sheath members with tips shaped and dimensioned to reduce trauma upon insertion.

2. Description of the Prior Art

In the field of interventional radiology, as well as other medical fields requiring both vascular and non-vascular access to the body, access to the interior of blood vessels must be obtained so that various devices, for example, guidewires, stents, balloons, filters and the like may be introduced into the blood vessel for medical purposes. In general, a device known as a sheath provides for desired access to the interior of the blood vessel.

A sheath generally consists of two concentric plastic tubes that are free to slide easily on each other. In accordance with current sheath designs, the inner and outer plastic tubes are in a "stepped" axial arrangement, that is, the inner plastic tube is longer than the outer plastic tube. The ends of the inner and outer plastic tubes are circular and are in a plane perpendicular to the longitudinal axis of the respective plastic tubes. This design creates a "step" at the ends of the inner and outer plastic tubes. A "step" is formed at the end of the inner plastic tube and the guidewire by the difference in the guidewire outer diameter (OD) and the OD of the end of the inner plastic tube. The length of the "step" is equal to one-half of the difference between the OD at the end of the inner plastic tube and the guidewire OD. A similar "step" is formed at the end of the outer plastic tube. The two "steps" may be of different lengths. In effect, the "steps" are merely radial discontinuities due to the diameter differences at the two "step" locations.

In use, a needle is generally used to obtain access to the interior of the blood vessel. A guidewire is inserted into the blood vessel through the needle and the needle is removed. The two plastic tubes of the sheath are then threaded over the guidewire and forced axially against the flesh of the patient until the tubes are inside the blood vessel. When the inner sheath reaches the patient, a pronounced stop of the insertion is detected by the physician. The stop is due to the radial discontinuity at the "step" between the guidewire OD and the end of the inner plastic tube. To force the inner plastic tube sheath into the hole created by the needle point, a significant axial force must be applied by the physician. The magnitude of the force depends, in part, on the geometry of the "step" and the elastic modulus of the flesh and the plastic tubes. In effect, forcing the sheath into the flesh is akin to creating an interference fit in a pair of cylinders. In an interference fit, a first cylinder is inserted within a second cylinder, wherein the second cylinder has an inner diameter that is slightly smaller than the OD of the first cylinder. Depending on the magnitude of the "step" and the elastic properties of the materials, a substantial axial force is required to produce an interference fit in this manner.

With the foregoing in mind, those skilled in the art will appreciate that current sheath designs have shortcomings that must be addressed. The present invention provides a sheath overcoming the shortcomings of prior sheaths.

SUMMARY OF THE INVENTION

It is, therefore, an object of the present invention to provide a sheath shaped and dimensioned for reducing trauma and easing insertion thereof. The sheath includes an inner sheath member. The inner sheath member includes an inner sheath tip having a primary bevel and a circumferential conical surface, wherein the primary bevel of the inner sheath member extends diametrically across the inner sheath member and the inner sheath tip is formed with a long distal end that extends further than a diametrically opposed short distal end, and the long distal end includes an arc length or point. An outer sheath member is shaped and dimensioned to fit around the inner sheath member in a manner permitting relative movement. The outer sheath member includes an outer sheath tip having a primary bevel and a circumferential conical surface, and wherein the primary bevel of the outer sheath member extends diametrically across the outer sheath member and the outer sheath tip is formed with a long distal end that extends further than a diametrically opposed short distal end and the long distal end includes an arc length.

It is also an object of the present invention to provide a sheath wherein the conical surface of the inner sheath member varies between the long distal end which has a first cone angle relative to a longitudinal axis of the inner sheath member and the short distal end which has a second cone angle relative to the longitudinal axis of the inner sheath member, and the first cone angle is less than the second cone angle, and the conical surface of the outer sheath member varies between the long distal end which has a first cone angle relative to a longitudinal axis of the outer sheath member and the short distal end which has a second cone angle relative to the longitudinal axis of the outer sheath member, and the first cone angle is less than the second cone angle.

It is another object of the present invention to provide a sheath wherein the primary bevel of the outer sheath member is formed at an angle of approximately 19.855° to approximately 35.8° relative to a longitudinal axis of the outer sheath member, and the primary bevel of the inner sheath member is formed at an angle of approximately 17.23° to approximately 31.8° relative to a longitudinal axis of the inner sheath member.

It is a further object of the present invention to provide a sheath wherein the conical surface of the outer sheath member varies between the long distal end which has a cone angle of approximately 5.29° relative to a longitudinal axis of the outer sheath member and the short distal end which has a cone angle of approximately 19.855° to approximately 35.8° relative to the longitudinal axis of the outer sheath member, and the conical surface of the inner sheath member varies between the long distal end which has a cone angle of approximately 2.92° relative to a longitudinal axis of the inner sheath member and the short distal end which has a cone angle of approximately 17.23° to approximately 31.8° relative to the longitudinal axis of the inner sheath member.

It is also an object of the present invention to provide a sheath wherein the sheath is composed of a plastic material.

It is another object of the present invention to provide a sheath wherein the inner sheath member is shaped and dimensioned to fit about a guidewire in a manner permitting relative movement.

It is a further object of the present invention to provide a sheath wherein the conical surface of the inner sheath member has a minimum cone angle of between approximately 2° and approximately 60°, the conical surface of the outer sheath member has a minimum cone angle of between approximately 2° and approximately 60°, the primary bevel of the inner sheath member is formed at an angle of between approximately 15° and approximately 60°, and the primary bevel of the outer sheath member is formed at an angle of between approximately 15° and approximately 60°.

It is also an object of the present invention to provide a sheath wherein the conical surface of the inner sheath member has a minimum cone angle which differs from a minimum cone angle of the conical surface of the outer sheath member, and the primary bevel of the inner sheath member is formed at an angle which differs from an angle of the primary bevel of the outer sheath member.

Other objects and advantages of the present invention will become apparent from the following detailed description when viewed in conjunction with the accompanying drawings, which set forth certain embodiments of the invention.

DESCRIPTION OF THE INVENTION

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1, 2, 3A, 3B and 4, a sheath 10 in accordance with the present invention is disclosed. The sheath 10 is designed to effectively remove the undesirable "steps" encountered in conventional sheaths by using pointed, rather than blunt ends, at the ends of the inner and outer sheath members (or tubes) 12, 14. The pointed ends provide the same overall radial deformation as conventional sheath members. However, the effect of the step is greatly minimized by distributing the radial deformations along the small axial length of the pointed tip 13, 15 at the respective ends of the inner and outer sheath members 12, 14.

By using pointed tip ends on the inner and outer sheath members 12, 14, the magnitude of the force required to insert the inner and outer sheath members 12, 14 through tissue is greatly reduced since the total radial deformation at the "step" is spread incrementally along the length of the pointed tips 13, 15 on the inner and outer sheath members 12, 14. Reducing the sheath insertion force results in much better control of the sheath 10 by the physician, with subsequently less trauma encountered by the patient.

As briefly mentioned above, the sheath 10 is composed of an inner sheath member 12 shaped and dimensioned to fit around a guidewire 16 and an outer sheath member 14 shaped and dimensioned to fit about the inner sheath member 12. The inner sheath member 12 and the outer sheath member 14 are preferably formed from a suitable plastic material, for example, TEFLON (a polytetrafluoroethylene manufactured by DuPont), although other materials may be used without departing from the spirit of the present invention. While specific dimensions are disclosed below in describing a preferred embodiment of the present invention, those skilled in the art will certainly appreciate the guidewire, inner sheath member and outer sheath member may be made in various shapes and sizes without departing from the spirit of the present invention. The components may also be made of various materials without departing from the spirit of the present invention. What is important is that the inner sheath member 12 have an inner diameter only slightly larger than the outer diameter of the guidewire 16 such that the inner sheath member 12 fits thereabout while permitting relative movement therebetween and that the outer sheath member 14 have an inner diameter only slightly larger than the outer diameter of the inner sheath member 12 such that the outer sheath member 14 fits thereabout while permitting relative movement therebetween.

As briefly mentioned above, the inner sheath member 12 and outer sheath member 14 include pointed tips 13, 15 shaped to reduce trauma during insertion of the sheath 10. With this in mind, the inner sheath member 12 includes an inner sheath tip 18 and the outer sheath member 14 includes an outer sheath tip 20. As will be described below in greater detail, both the inner and outer sheath tips 18, 20 are formed with a primary bevel 22, 24 and a circumferential conical surface 26, 28.

With regard to the outer sheath tip 20, it is formed with a primary bevel 24 extending diametrically across the pointed tip 15 of the outer sheath member 14. As will be discussed below in greater detail, the primary bevel 24 preferably conforms with the maximum cone angle along the outer sheath tip 20. Because of the primary bevel 24, the outer sheath tip 20 is formed with a long distal end 30 that extends further than the diametrically opposed short distal end 32, with the remainder of the outer sheath tip 20 being positioned between the long distal end 30 and the short distal end 32 as the outer sheath tip 20 extends about its circular profile. As a result, the primary bevel 24 extends from the tip 33 of the short distal end 32 to the tip 35 of the long distal end 30. In accordance with a preferred embodiment of the present invention the primary bevel 24, or bevel angle ($\alpha$), will vary depending upon the desired arc length as discussed below and as shown with reference to the charts presented in FIGS. 5A and 5B. In accordance with a preferred embodiment of the present invention, the bevel angle ranges from approximately 19.855° to approximately 35.8° relative to the longitudinal axis of the outer sheath member 14.

More particularly, and with reference to FIGS. 1, 2, 3A, 3B and 4, the outer sheath tip 20 includes a conical surface 28, with a cone angle (β), formed about the circumference of the outer sheath tip 20. The conical surface 28 varies between the long distal end 30 that has a cone angle (that is, minimum cone angle) of approximately 5.29° relative to the longitudinal axis of the outer sheath member 14 and the short distal end 32 which has a cone angle (that is, maximum cone angle) of approximately 19.855° to approximately 35.8° relative to the longitudinal axis of the outer sheath member 14. In accordance with a preferred embodiment, the bevel angle α(γ) is set to substantially conform with the maximum cone angle β at the short distal end 32. With regard to the cone angles of the outer sheath tip 20 between the long distal end 30 and the short distal end 32, it varies between approximately 5.29° and approximately 19.855° to approximately 35.8° as the cone angle transitions from a high of approximately 19.855° to approximately 35.8° adjacent the short distal end 32 and a low of approximately 5.29° adjacent the long distal end 30.

In view of the different cone angles along the circumference of the outer sheath tip 20, the length of the outer sheath tip 20 along the conical surface 28 (that is, the cone length) changes depending upon the cone angle at that position. In particular, and considering an outer sheath member 14 having an inner radius of 0.0195 inches and an outer radius of 0.0245 inches, the outer sheath tip 20 adjacent the long distal end 30 will have a length of approximately 0.054 inches and the outer sheath tip 20 adjacent the short distal end 32 will have a length of approximately 0.007 inches to approximately 0.014 inches. However, and as those skilled as in the art will certainly appreciate, various dimensions may be employed once one determines the desired arc length based upon the desired stiffness characteristics.

In an effort to increase the strength of the outer sheath tip 20 and to prevent bending thereof, it is desirable to provide an arc length (or sharp edge) 31 at the tip 35 of the long distal end 30 of the outer sheath tip 20. In particular, an arc length 31 is considered to be an edge at the free end of the long distal end 30 that extends about an arc and the arc lies in a plane that is substantially perpendicular and transverse to the longitudinal axes of the outer sheath member 14. The arc length 31 is achieved by grinding or molding the long distal end 30 perpendicular to the longitudinal axis of the outer sheath member 14 and subsequently grinding or molding the conical surface 28 along the arc length 31 to provide a sharp edge along the arc length 31. With this in mind, and in accordance with a preferred embodiment, the bevel angle, outer sheath member 14 thickness and cone angle at the long distal end 30 are selected such that the long distal end 30 ends before the plane defined by the location where the bevel angle crosses the outer sheath member 14 at the tip 35 along the upper side 37 of the long distal end 30.

It should be understood the arc length 31 is a function of the bevel angle. More particularly, from the figure, it is evident that the arc length 31 of the sharp edge ACB (that is, the points along the arc length) is a function of the angle γ. It is contemplated the sharp edge defined along the arc ACB may degenerate to a point at C. As a result, the same design and manufacturing procedures used to create a sheath with a sharp edge may be employed in the creation of a pointed sheath. The length of the circular arc portion of the arc length, S(γ), can be calculated using the following equation, where r=the inner radius of the sheath being designed and R=the outer radius of the sheath being designed:

$$S(\gamma) = \pi r(90 - \gamma)/90 \quad (2A)$$

Figure 1:
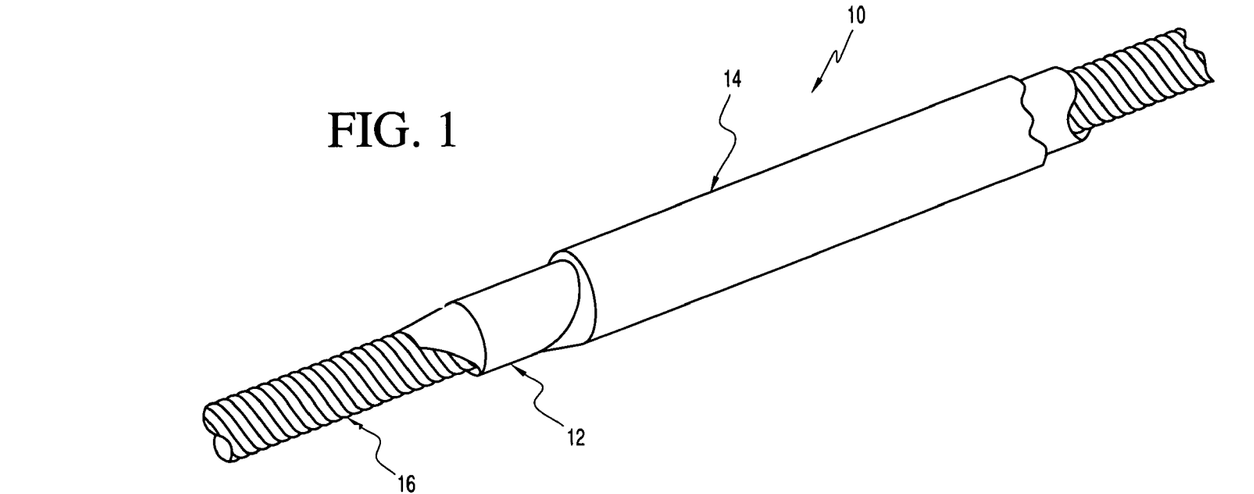
FIG. 1 is a perspective view of a sheath in accordance with the present invention.
Figure 2:
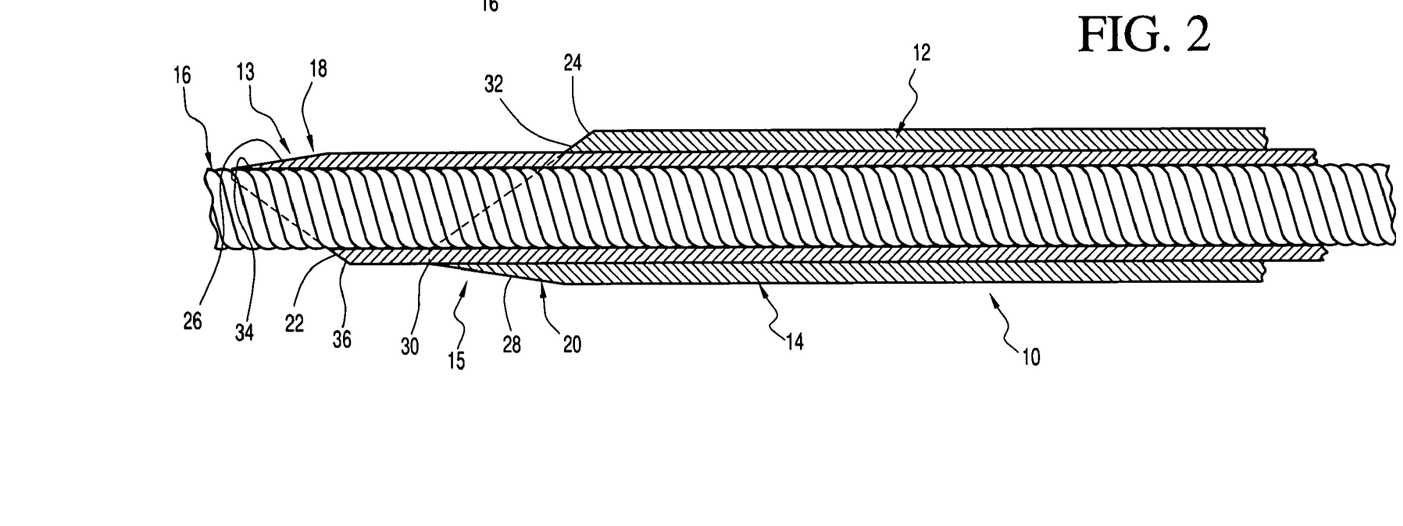
FIG. 2 is a cross sectional view of the sheath shown in FIG. 1.
Figure 3A:
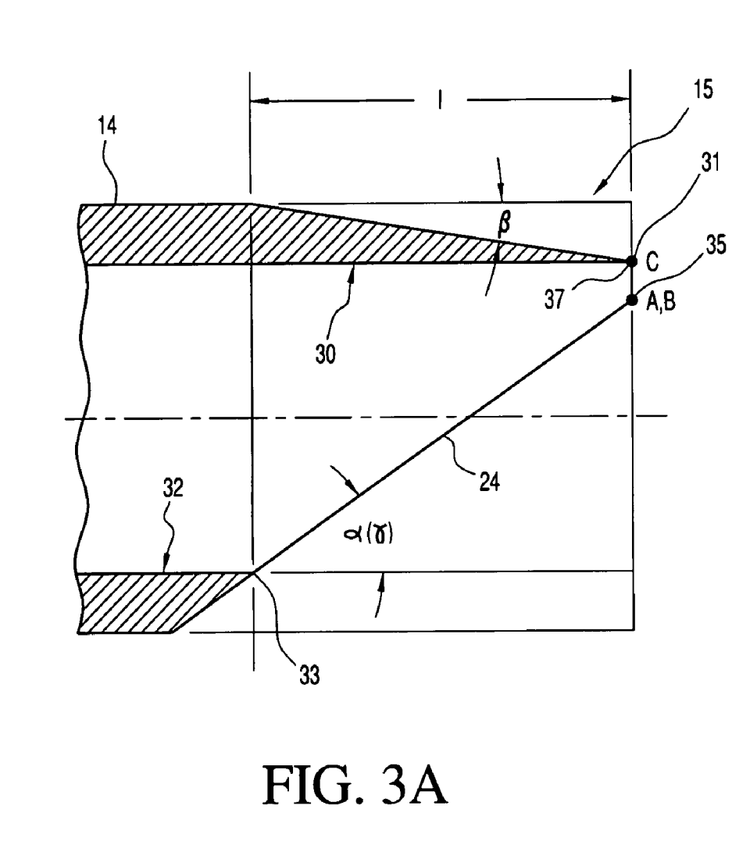
FIGS. 3A and 3B are respectively a cross sectional view of an outer sheath member in accordance with the present invention and a front plan view of the outer sheath member shown in FIG. 3A.
Figure 3B:
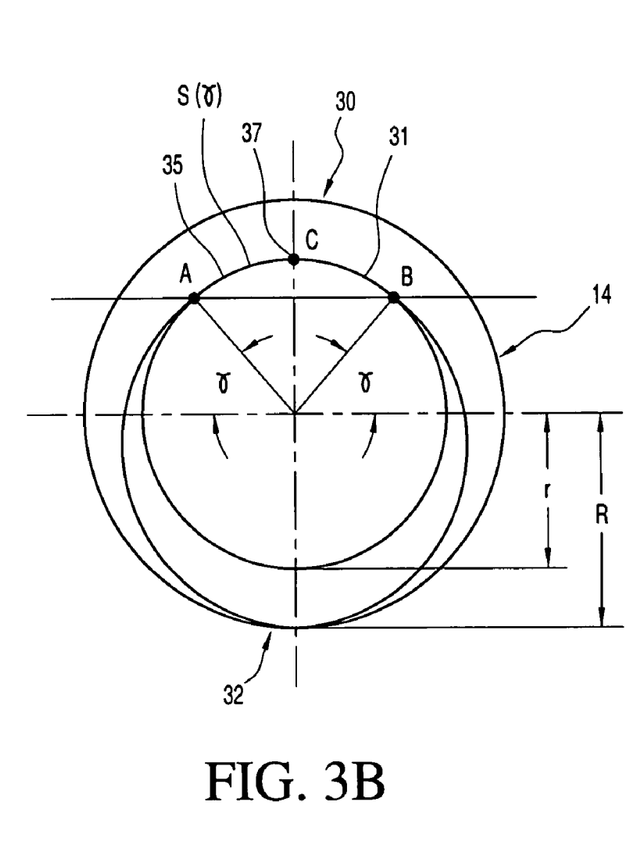
Figure 4:
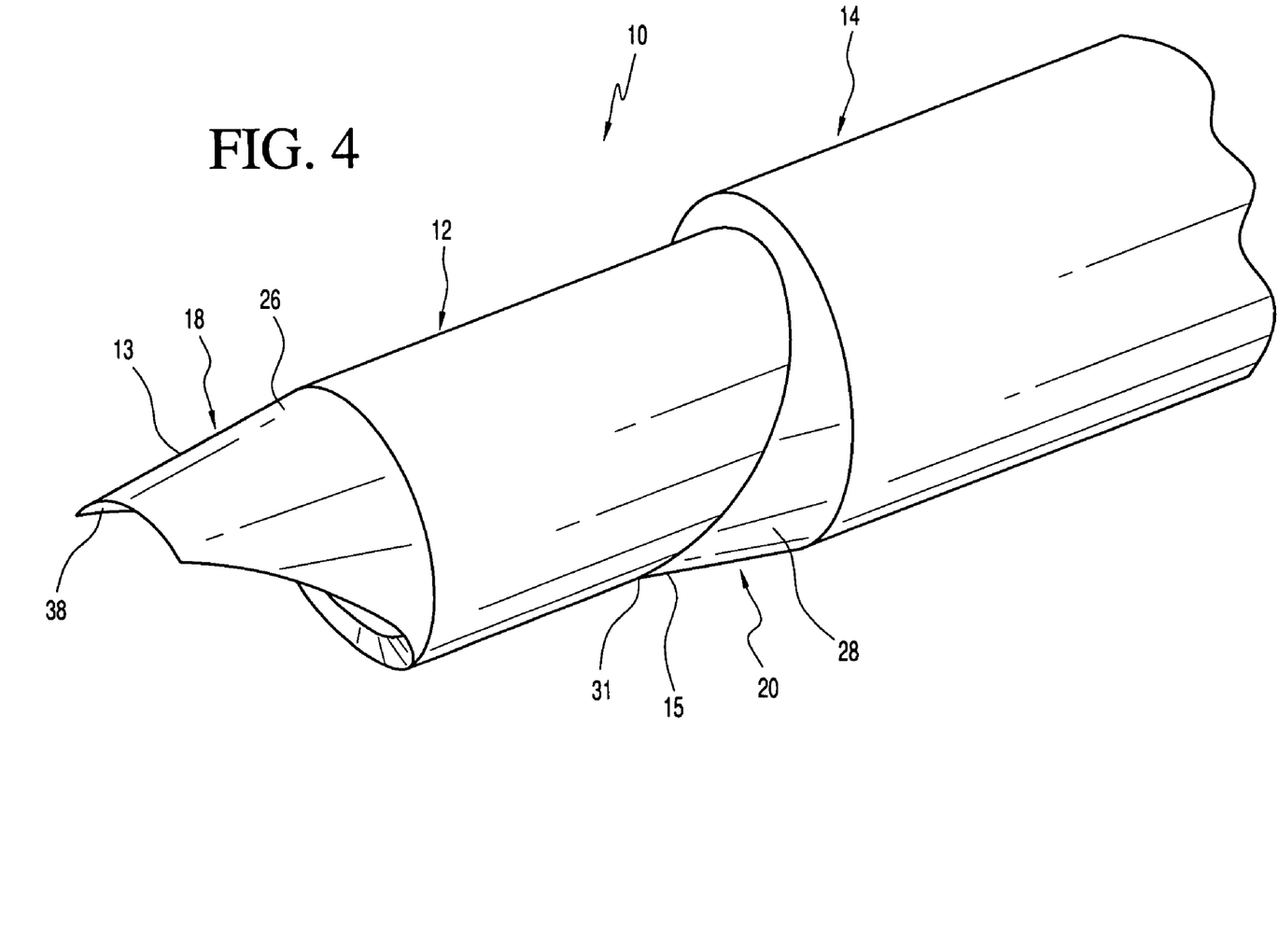
FIG. 4 is a detailed perspective view of the sheath shown in FIG. 1.
Figure 5A:
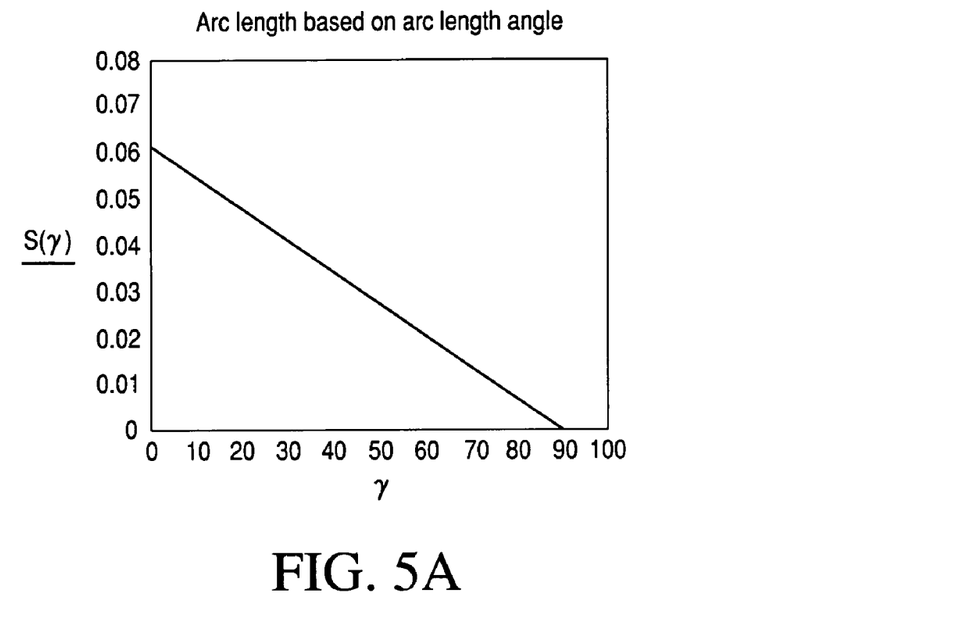
FIGS. 5A and 5B are respectively graphical representations of the arc length as a function of the arc length angle and the bevel angle as a function of the arc length angle for the outer sheath member.

A graph of S(γ) vs. γ is given in FIG. 5A for the parameters selected for this example. Further, and in accordance with a preferred embodiment of the present invention, it is also evident from the figure that the bevel angle α(γ), that is, the cone angle, β, at the short distal end 32 of the outer sheath 14, is also a function of the angle γ. The bevel angle can be calculated using the following equation:

$$\alpha(\gamma) = \arctan(r(1 + \sin \gamma)/l) \quad (2B)$$

Equations 2A and 2B are valid for all values of α from −90 to +90 degrees.

Figure 5B:
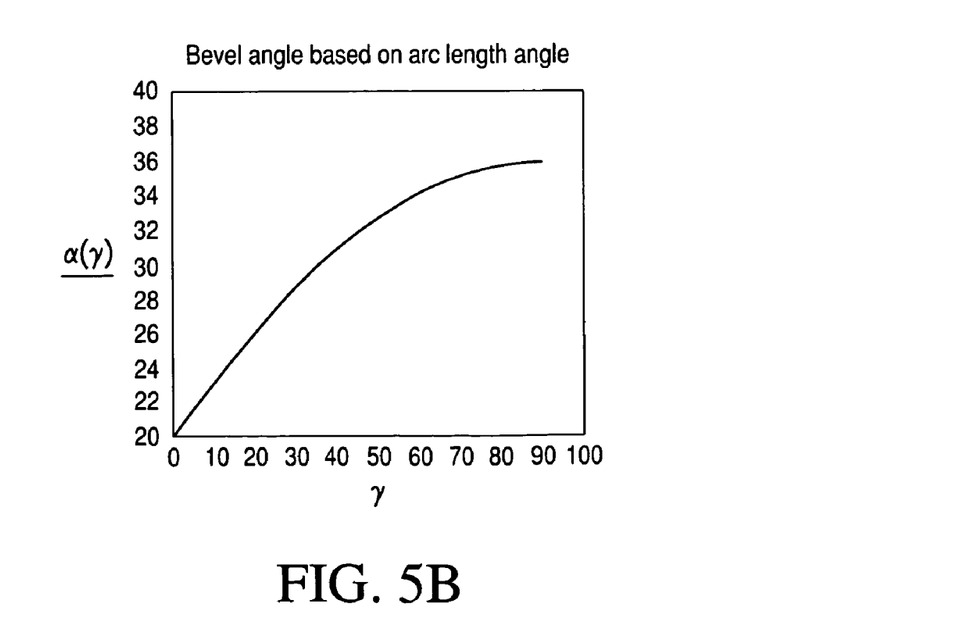

A graph of α(γ) vs. γ is given in FIG. 5B for the parameters selected for this example.

From the graphs shown in FIGS. 5A and 5B, it is evident that for γ=0, the arc length (ACB) 31 is a semicircle and the bevel angle is 19.8 degrees and S(γ)=0.062". Also, for γ=90 degrees, the arc length (ACB) 31 is equal to zero which means that a point would exist at location C in FIG. 3C and the bevel angle (that is, α(γ)) is 35.8 degrees.

Hence, for values of γ from zero to, but not including, 90 degrees an arc length, S (γ), as shown in the design curve is produced. For γ=90 degrees, the arc length degenerates to a point, i.e., S(γ)=0, which is positioned at the tip 35 along the upper side 37 of the long distal end 30. This is valid for all values of the parameters r (that is, the inner radius of the outer sheath 14), and γ used to develop the design curves. Using equations 2A and 2B, the sheath designer can develop his own charts 5A and 5B for any sheath geometry.

Note that when using plastic sheath materials that are strong enough to prevent bending of the pointed end of the sheath and yet flexible enough to have satisfactory performance, designs with pointed ends (i.e., γ=90°) are suitable. However, for sheath materials in which bending of the point will occur, the unsatisfactory bending of the tip of the sheath may be eliminated by using values of γ which are less than 90 degrees.

Using the equations given above, the distal ends of both the outer sheath member 14 and the inner sheath member 12 may be designed to satisfactorily resist bending and eliminate the "radial steps" used currently in commercially available sheaths. Elimination of the "radial steps" results in improved sheath control for the physician and reduced trauma for the patient.

With regard to the inner sheath tip 18, it is also formed with a primary bevel (as defined above with regard to the outer sheath member) 22 extending diametrically across the pointed tip 13 of the inner sheath member 12. Because of the primary bevel 22, the inner sheath tip 18 is formed with a long distal end 34 that extends further than the diametrically opposed short distal end 36, with the remainder of the inner sheath tip 18 being positioned between the long distal end 34 and the short distal end 36 as the inner sheath tip 18 extends about its circular profile. Enhanced performance is achieved by positioning the long distal end 34 of the inner sheath tip 18 diametrically opposed to the long distal end 30 of the outer sheath tip 20, and similarly positioning the short distal end 36 of the inner sheath tip 18 diametrically opposed to the short distal end 32 of the outer sheath tip 20.

In accordance with a preferred embodiment of the present invention the primary bevel 22, or bevel angle (α) (which conforms with the cone angle, β, of the short distal end 32 of the inner sheath 12), is formed at an angle of approximately 17.23° to approximately 31.8° relative to the longitudinal axis of the inner sheath member 14. In practice, the designer will select the desired inner and outer diameters, as well as the tip lengths and wire diameters, and the remaining parameters are calculated in the manner discussed below.

More particularly, the inner sheath tip 18 includes a conical surface 26, with a cone angle (β), formed about the circumference of the inner sheath tip 18. The conical surface 26 varies between the long distal end 34 which has a cone angle (that is, minimum cone angle) of approximately 2.92° in accordance with a preferred embodiment relative to the longitudinal axis of the inner sheath member 12 and the short distal end 36 which has a cone angle (that is, maximum cone angle) of approximately 17.23° to approximately 31.8° in accordance with a preferred embodiment relative to the longitudinal axis of the inner sheath member 12. With regard to the conical surface 26 of the inner sheath tip 18 between the long distal end 34 and the short distal end 36, it varies between approximately 2.92° and approximately 17.23° to approximately 31.8° as the cone angle transitions from a high of approximately 17.23° to approximately 31.8° adjacent the short distal end 36 and a low of approximately 2.92° adjacent the long distal end 34.

In view of the different cone angles along the circumference of the inner sheath tip 18, the length of the inner sheath tip 18 along the conical surface 26 (that is, the cone length) changes depending upon the cone angle at that position. In particular, and considering an inner sheath member 12 having an inner radius of 0.01675 inches and an outer radius of 0.0195 inches, the inner sheath tip 18 adjacent the long distal end 34 will have a length of approximately 0.054 inches and the inner sheath tip 18 adjacent the short distal end 36 will have a length of approximately 0.0044 inches to approximately 0.0088 inches.

As with the outer sheath member 14, and in an effort to increase the strength of the inner sheath tip 18 and to prevent bending thereof, it is desirable to provide an arc length 38 at the long distal end 34 of the inner sheath tip 18. The arc length 31 is achieved by grinding or molding the long distal end 34 perpendicular to the longitudinal axis of the inner sheath member 12 and subsequently grinding or molding the cone angle along the arc length to provide a sharp edge along the arc length. With this in mind, and in accordance with a preferred embodiment, the bevel angle, sheath member thickness and cone angle at the long distal end 34 are selected such that the long distal end 34 ends before the plane defined by the location where the bevel angle crosses the inner sheath member 12 at the long distal end 34.

Although a preferred embodiment of the inner sheath member 12 and outer sheath member 14 are presented above, it is contemplated the conical surface 26 of the inner sheath member 12 will have a minimum cone angle of between approximately 2° and approximately 60°, the conical surface 28 of the outer sheath member 14 will have a minimum cone angle of between approximately 2° and approximately 60°, the primary bevel 22 of the inner sheath member 12 will be formed at an angle of between approximately 15° and approximately 60°, and the primary bevel 24 of the outer sheath member 14 will be formed at an angle of between approximately 15° and approximately 60°. In addition, and as discussed above, it is also contemplated the conical surface 26 of the inner sheath member 12 may have a cone angle which differs from a cone angle of the conical surface 28 of the outer sheath member 14, and the primary bevel 22 of the inner sheath member 12 may be formed at an angle which differs from an angle of the primary bevel 24 of the outer sheath member 14.

Referring to the Figures, the present sheath 10 employs the sheath design geometry principles. The objective is to produce a sheath with tapered, sharp cutting edges which will penetrate the tissue more easily than sheaths of conventional design. As discussed above, a simple beveled point alone yields tapered surfaces along the outer sheath member which produce a force which must be overcome to insert the outer sheath member. To reduce the magnitude of this insertion force, a conical surface 26, 28, or point, is added to remove a portion of the primary bevel 22, 24. The resulting beveled/conical surface provides sharp tissue cutting edges along its entire tapered length.

In accordance with a preferred embodiment, the beveled/conical surface is generated by first grinding the primary bevel then grinding the conical surface (or reversing the grinding procedure). To prevent bending of the tip, the grinding may be controlled to provide either a feathered edge having a theoretical radial thickness equal to zero or an edge having a prescribed radial thickness and for a prescribed circumferential arc length. It is contemplated, that in production the sheath geometry would be molded.

The combined conical surface and primary bevel reduces the projected area of the beveled portion greatly when compared with merely using beveled points on the outer sheath members. In addition, the combined conical surface and primary bevel yields a cutting edge at the outer surface of the inner and outer sheath tips, which will cut rather than tear or displace tissue during insertion into the patient and should reduce patient trauma.

It should be appreciated that although the sheath designs considered in the examples given above are valid for designs in which the angle, γ, only varies from zero to 90°, equations 2A and 2B are valid for all values of the angle γ from −90° to =90°. Hence, using the equations given above, the outer sheath tip 20 of the outer sheath member 14 may be designed to have an unchanging taper, that is, cone angle, for example, of β=5.29°, for the entire 360° of the distal end. In accordance with such a design, the β=5.29° taper would be perpendicular to the axis of the sheath 10. Alternatively, the distal end may be pointed with a 5.29° cone angle and be beveled at 35.8° from the axis of the outer sheath member 14. Further, the distal end of the outer sheath member 14 may be designed from any geometry between these two extremes. The design graphs for these distal ends are give in FIGS. 6A, 6B, 7A and 7B, for the inner and outer sheath members 12, 14 considered herein.

Included herein with reference to FIGS. 6A, 6B, 7A and 7B, is a summary of the sheath design equations and design graphs for the inner sheath member 12 and the outer sheath member 14 in which the design covers the complete range of the angle, γ, from −90° to +90°, rather than only 0° to +90° as is disclosed above with regard to an alternate embodiment. By including the extended range of the angle, γ, (that is, −90° to +90°), it is contemplated the present disclosure covers possible design variations from a 360° conical taper angle β to an arc length geometry . . . and finally, to a sharp point.

Figure 6A:
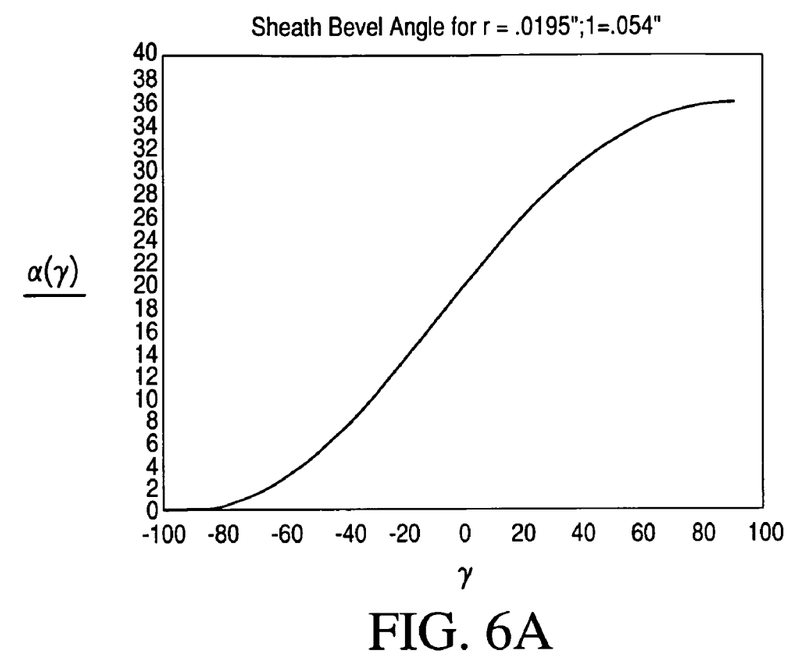
FIGS. 6A and 6B are respectively graphical representations of the bevel angle as a function of the arc length and the arc length as a function of the arc length angle for the outer sheath member.
Figure 6B:
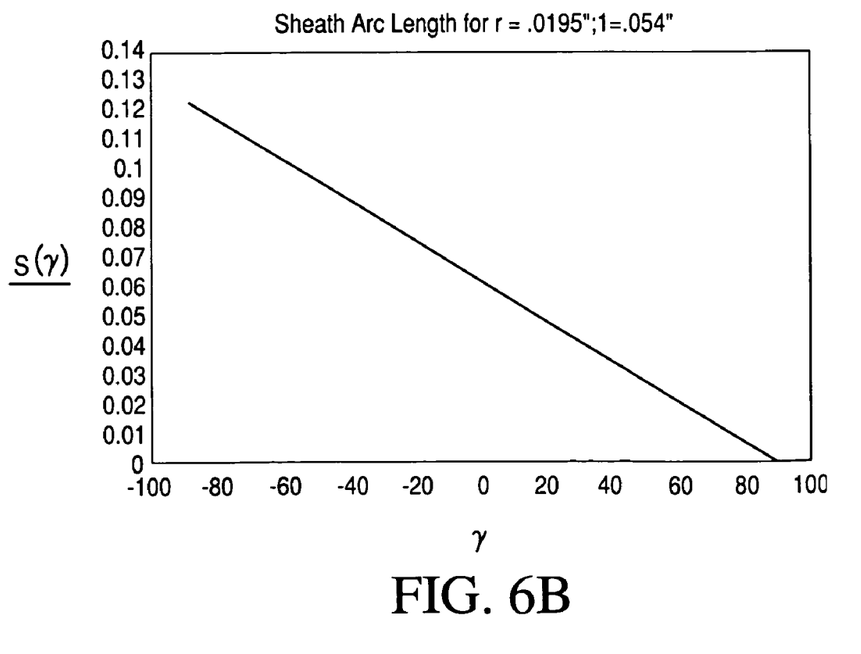

Referring now to FIGS. 6A and 6B, and in accordance with a preferred embodiment of the present invention, the bevel angle α (γ), based on arc angle, γ is defined as follows:

$$r := .0195 \quad l := .054 \quad R := .0245$$

$$\gamma := -90, -88 \ldots 90$$

$$\alpha(\gamma) := \operatorname{atan}\left[r \cdot \left(\frac{1 + \sin(\gamma \cdot \deg)}{l}\right)\right] \cdot \frac{180}{\pi}$$

The arc length, ACB, at the tip of the bevel, S(γ), based on the arc angle, γ, is defined as follows:

$$S(\gamma) := \frac{\pi \cdot r \cdot (90 - \gamma)}{90}$$

The sheath cone angle, β, based on outer sheath member 14 outer radius, R, inner radius, r, and cone angle length parallel to the center line of the sheath, l, is defined as follows with the values for γ, α, (γ), S(γ) listed as they are presented in graphical representation in FIGS. 6A and 6B:

$$\beta := \operatorname{atan}\left(\frac{R-r}{l}\right) \cdot \frac{180}{\pi}$$

$$\beta = 5.29 \text{ degrees}$$

| γ = | α(γ) = | S(γ) = |
|---|---|---|
| −90 | 0 | 0.123 |
| −88 | 0.013 | 0.121 |
| −86 | 0.05 | 0.12 |
| −84 | 0.113 | 0.118 |
| −82 | 0.201 | 0.117 |
| −80 | 0.314 | 0.116 |
| −78 | 0.452 | 0.114 |
| −76 | 0.615 | 0.113 |
| −74 | 0.801 | 0.112 |
| −72 | 1.013 | 0.11 |
| −70 | 1.248 | 0.109 |
| −68 | 1.506 | 0.108 |
| −66 | 1.788 | 0.106 |
| −64 | 2.093 | 0.105 |
| −62 | 2.42 | 0.103 |
| −60 | 2.77 | 0.102 |

Note the two graphs shown with reference to FIG. 6 can be used to design 1) sheaths having a 360° conical taper of β=5.29°, 2) sheaths having a conical point and a bevel angle α(γ), of 35.8°, and 3) all geometries between these two extremes.

Consider the following for and outer sheath for which R=0.0245", r=0.0195" and l=0.054" (as the information is presented in FIGS. 6A and 6B) for angle γ=−90°

$$S(\gamma) := \frac{\pi \cdot r \cdot (90 - \gamma)}{90}.$$

S(−90)=0.123
   inches, i.e., the length of the sharp edge is equal to the entire circumference of a circle which has a radius equal to the inner radius of the outer sheath member 14 (i.e., r=0.0195"). Hence, the entire 360° sharp edge has a cone angle of β=5.29°.

Further, for γ=−90°

$$\alpha(\gamma) := \operatorname{atan}\left[r \cdot \left(\frac{1 + \sin(\gamma \cdot \deg)}{l}\right)\right] \cdot \frac{180}{\pi}$$

α(−90)=0
   degrees, i.e., the angle of the bevel at the end of the outer sheath member 14 is equal to zero. Hence, the end of the outer sheath member 14 is perpendicular to the longitudinal axis of the outer sheath member 14 and the entire 360° sharp edge of the outer sheath member 14 has a cone angle equal to β=5.29° since no bevel angle exists at γ=90°, i.e., α(−90)=0.

Let's consider now the geometry of the distal end of the outer sheath member 14 for γ=90°

$$S(\gamma) := \frac{\pi \cdot r \cdot (90 - \gamma)}{90}$$

S(90)=0
   inches, i.e., the sharp edge at the end of the outer sheath member 14 has degenerated to point since the length of the sharp edge, S(90), is equal to zero.

Further, for γ=90°

$$\alpha(\gamma) := \operatorname{atan}\left[r \cdot \left(\frac{1 + \sin(\gamma \cdot \deg)}{l}\right)\right] \cdot \frac{180}{\pi}$$

α(90)=35.838
   degrees, i.e., the bevel angle at the distal end of the outer sheath member 14 is 35.8° and the cone angle, β, at the distal end is equal to 5.29°.

The cone angle, β, may be calculated as follows:

$$\beta := \operatorname{atan}\left(\frac{R-r}{l}\right) \cdot \frac{180}{\pi}$$

$$\beta = 5.29 \text{ degrees}$$

Hence, using the equations given above, the distal end of the outer sheath member 14 may be designed to have an unchanging taper of β=5.29° for the entire 360° of the distal end. Alternatively, the distal end of the outer sheath member 14 may be pointed with a β=5.29° cone angle and be beveled at 35.8°. Further, the distal end of the outer sheath member 14 may be designed for any geometry between these two extremes by using the graphs. Using the equations given above, the designer may easily develop his own design graphs for use with any desired tubing size.

Figure 7A:
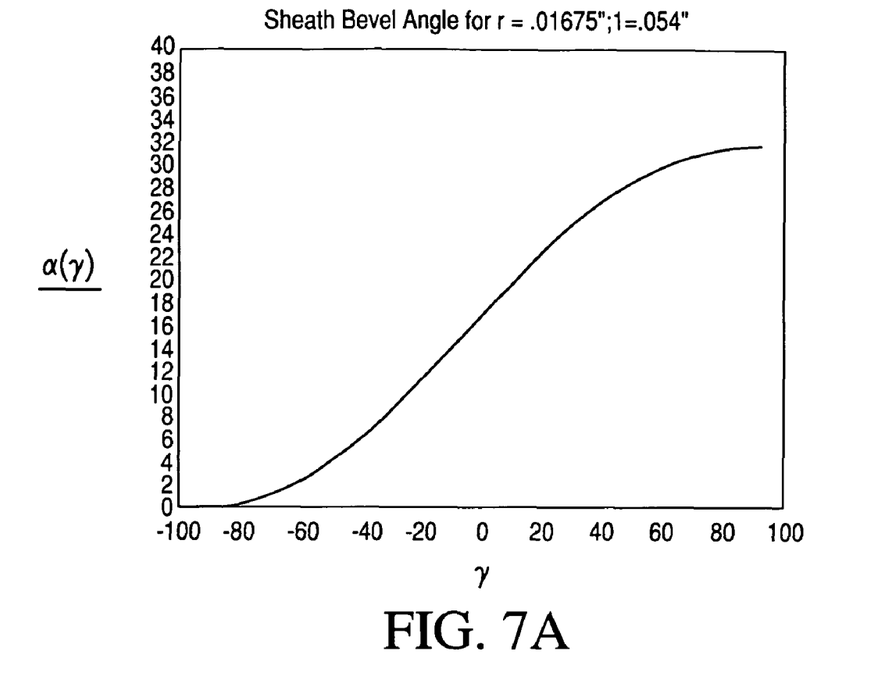
FIGS. 7A and 7B are respectively graphical representations of the bevel angle as a function of the arc length and the arc length as a function of the arc length angle for the outer sheath member.
Figure 7B:
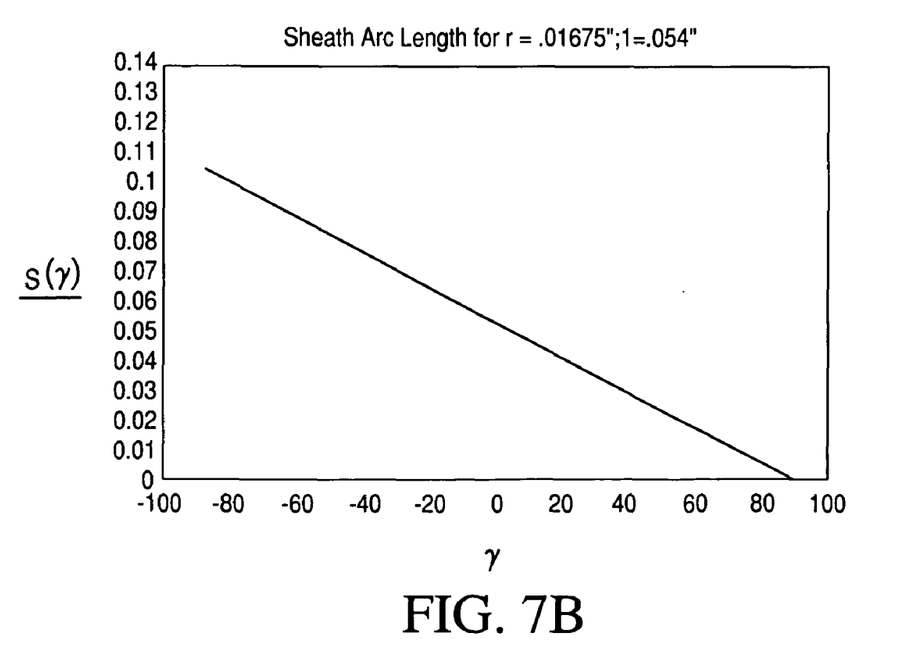

Referring to FIGS. 7A and 7B, the design of the inner sheath member 12 may be achieved in a similar manner. In particular, for a bevel angle, α(γ), based on arc angle, γ:

$$r := .01675 \quad l := .054 \quad R := .0195$$

$$\gamma := -90, -88 \ldots 90$$

$$\alpha(\gamma) := \operatorname{atan}\left[r \cdot \left(\frac{1 + \sin(\gamma \cdot \deg)}{l}\right)\right] \cdot \frac{180}{\pi}$$

The arc length, ACB, at the tip of the bevel, S(γ), based on arc angle, γ, is calculated as follows:

$$S(\gamma) := \frac{\pi \cdot r \cdot (90 - \gamma)}{90}$$

Sheath cone angle, β, based on sheath tubing outer radius, R, inner radius, r, and cone angle length parallel to the centerline of the sheath, l, is calculated as follows with the values for γ, α, (γ), S(γ) listed as they are presented in the graphical representation of FIGS. 7A and 7B.

$$\beta := \operatorname{atan}\left(\frac{R-r}{1}\right) \cdot \frac{180}{\pi}$$

$$\beta = 2.915 \text{ degrees}$$

| $\gamma =$ | $\alpha(\gamma) =$ | $S(\gamma) =$ |
|---|---|---|
| −90 | 0 | 0.105 |
| −88 | 0.011 | 0.104 |
| −86 | 0.043 | 0.103 |
| −84 | 0.097 | 0.102 |
| −82 | 0.173 | 0.101 |
| −80 | 0.27 | 0.099 |
| −78 | 0.388 | 0.098 |
| −76 | 0.528 | 0.097 |
| −74 | 0.688 | 0.096 |
| −72 | 0.87 | 0.095 |
| −70 | 1.072 | 0.094 |
| −68 | 1.294 | 0.092 |
| −66 | 1.536 | 0.091 |
| −64 | 1.798 | 0.09 |
| −62 | 2.079 | 0.089 |
| −60 | 2.38 | 0.088 |

The two graphs with reference to FIGS. 7A and 7B can be used to design 1) sheaths having a 360° conical taper of β=2.92°, 2) sheaths having a conical point and a bevel angle α(γ), of 31.8°, and 3) all geometries between these two extremes.

Consider the following for the outer sheath for which R=0.0195″, r=0.1675″ and 1=0.054″ (as the information is presented in FIGS. 7A and 7B) for angle γ=−90°:

$$S(\gamma) := \frac{\pi \cdot r \cdot (90 - \gamma)}{90}$$

S(−90)=0.105
    inches, i.e., the length of the sharp edge is equal to the entire circumference of a circle which has a radius equal to the inner radius of the outer sheath (i.e., r=0.01675″). Hence, the entire 360° sharp edge has a cone angle of β=2.92°.

Further, for γ=−90°

$$\alpha(\gamma) := \operatorname{atan}\left[r \cdot \left(\frac{1 + \sin(\gamma \cdot \deg)}{1}\right)\right] \cdot \frac{180}{\pi}$$

α(−90)=0
    degrees, i.e., the angle of the bevel at the end of the inner sheath member 12 is equal to zero. Hence, the end of the inner sheath member 12 is perpendicular to the longitudinal axis of the inner sheath member 12 and the entire 360° sharp edge of the inner sheath member 12 has a cone angle equal to β=2.92° since no bevel angle exists at γ=−90°, i.e., α(−90)=0.

Let's consider now the geometry of the distal end of the inner sheath member 12 for γ=90°

$$S(\gamma) := \frac{\pi \cdot r \cdot (90 - \gamma)}{90}$$

S(90)=0
    inches, i.e., the sharp edge at the end of the inner sheath member 12 has degenerated to point since the length of the sharp edge, S(90), is equal to zero.

Further, for γ=90°

$$\alpha(\gamma) := \operatorname{atan}\left[r \cdot \left(\frac{1 + \sin(\gamma \cdot \deg)}{1}\right)\right] \cdot \frac{180}{\pi}$$

α(90)=31.814
    degrees, i.e., the bevel angle at the distal end of the inner sheath member 12 is 31.8° and the cone angle, β, at the distal end is equal to 2.92°.

The cone angle, β, may be calculated as follows:

$$\beta := \operatorname{atan}\left(\frac{R-r}{1}\right) \cdot \frac{180}{\pi}$$

$$\beta = 2.915 \text{ degrees}$$

Hence, using the equations given above, the distal end of the inner sheath member 12 may be designed to have an unchanging taper of β=2.92° for the entire 360° of the distal end. Alternatively, the distal end of the inner sheath member 12 may be pointed with a β=2.92° cone angle and be beveled at 31.8°. Further, the distal end of the inner sheath member 12 may be designed for any geometry between these two extremes by using the graphs. Using the equations given above, the designer may easily develop his own design graphs for use with any desired tubing size.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A sheath shaped and dimensioned for reducing trauma and easing insertion thereof, the sheath comprising:
    an inner sheath member, the inner sheath member including an inner sheath tip having a primary bevel and a circumferential conical surface, wherein the primary bevel of the inner sheath member extends diametrically across the inner sheath member and the inner sheath tip is formed with a long distal end that extends further than a diametrically opposed short distal end, and the long distal end includes an arc length or point, wherein the arc length is an edge at a free end of the long distal end that extends about an arc and the arc lies in a plane that is substantially perpendicular and transverse to a longitudinal axis of the inner sheath member;
    an outer sheath member shaped and dimensioned to fit around the inner sheath member in a manner permitting relative movement, the outer sheath member including an outer sheath tip having a primary bevel and a circumferential conical surface, and wherein the primary bevel of the outer sheath member extends diametrically across the outer sheath member and the outer sheath tip is formed with a long distal end that extends further than a diametrically opposed short distal end and the long distal end includes an arc length, wherein the arc length is an edge at a free end of the long distal end that extends about an arc and the arc lies in a plane that is substantially perpendicular and transverse to a longitudinal axis of the outer sheath member;
    wherein the conical surface of the inner sheath member varies between the long distal end which has a first cone angle relative to a longitudinal axis of the inner sheath member and the short distal end which has a second cone angle relative to the longitudinal axis of the inner sheath member, and the first cone angle is less than the second cone angle, and the conical surface of the outer sheath member varies between the long distal end which has a first cone angle relative to a longitudinal axis of the outer sheath member and the short distal end which has a second cone angle relative to the longitudinal axis of the outer sheath member, and the first cone angle is less than the second cone angle.

2. A sheath according to claim 1, wherein the primary bevel of the outer sheath member is formed at an angle of approximately 19.855° to approximately 35.8° relative to a longitudinal axis of the outer sheath member, and the primary bevel of the inner sheath member is formed at an angle of approximately 17.23° to approximately 31.8° relative to a longitudinal axis of the inner sheath member.

3. A sheath according to claim 2, wherein the conical surface of the outer sheath member varies between the long distal end which has a cone angle of approximately 5.29° relative to a longitudinal axis of the outer sheath member and the short distal end which has a cone angle of approximately 19.855° to approximately 35.8° relative to the longitudinal axis of the outer sheath member, and the conical surface of the inner sheath member varies between the long distal end which has a cone angle of approximately 2.92° relative to a longitudinal axis of the inner sheath member and the short distal end which has a cone angle of approximately 17.23° to approximately 31.8° relative to the longitudinal axis of the inner sheath member.

4. A sheath according to claim 1, wherein the conical surface of the outer sheath member varies between a cone angle of approximately 5.29° relative to a longitudinal axis of the outer sheath member and a cone angle of approximately 19.855° to approximately 35.8° relative to the longitudinal axis of the outer sheath member, and the conical surface of the inner sheath member varies between a cone angle of approximately 2.92° relative to a longitudinal axis of the inner sheath member and a cone angle of approximately 17.23° to approximately 31.8° relative to the longitudinal axis of the inner sheath member.

5. A sheath according to claim 1, wherein the sheath is composed of a plastic material.

6. A sheath according to claim 1, wherein the inner sheath member is shaped and dimensioned to fit about a guidewire in a manner permitting relative movement.

7. A sheath according to claim 1, wherein the conical surface of the inner sheath member has a minimum cone angle of between approximately 2° and approximately 60°, the conical surface of the outer sheath member has a minimum cone angle of between approximately 2° and approximately 60°, the primary bevel of the inner sheath member is formed at an angle of between approximately 15° and approximately 60°, and the primary bevel of the outer sheath member is formed at an angle of between approximately 15° and approximately 60°.

8. A sheath according to claim 1, wherein the conical surface of the inner sheath member has a minimum cone angle which differs from a minimum cone angle of the conical surface of the outer sheath member, and the primary bevel of the inner sheath member is formed at an angle which differs from an angle of the primary bevel of the outer sheath member.

* * * * *